US011771683B2

(12) United States Patent
Dingemanse et al.

(10) Patent No.: US 11,771,683 B2
(45) Date of Patent: Oct. 3, 2023

(54) DOSING REGIMEN FOR A SELECTIVE S1P$_1$ RECEPTOR AGONIST

(71) Applicant: ACTELION PHARMACEUTICALS LTD, Allschwil (CH)

(72) Inventors: Jasper Dingemanse, Allschwil (CH); Matthias Hoch, Harston (GB); Andreas Krause, Allschwil (CH)

(73) Assignee: Actelion Pharmaceuticals Ltd, Allschwil (CH)

( * ) Notice: Subject to any disclaimer, the term of this patent is extended or adjusted under 35 U.S.C. 154(b) by 0 days.

(21) Appl. No.: 17/090,756

(22) Filed: Nov. 5, 2020

(65) Prior Publication Data

US 2021/0052555 A1    Feb. 25, 2021

Related U.S. Application Data

(62) Division of application No. 16/261,327, filed on Jan. 29, 2019, now Pat. No. 10,857,134, which is a division of application No. 15/534,929, filed as application No. PCT/EP2015/079208 on Dec. 10, 2015, now Pat. No. 10,220,023.

(51) Int. Cl.
*A61K 31/426* (2006.01)
*A61K 9/00* (2006.01)

(52) U.S. Cl.
CPC .......... *A61K 31/426* (2013.01); *A61K 9/0053* (2013.01)

(58) Field of Classification Search
CPC ..... A61K 31/426; A61K 9/0053; A61P 11/02; A61P 11/06; A61P 13/12; A61P 17/00; A61P 17/06; A61P 19/02; A61P 1/00; A61P 1/04; A61P 25/00; A61P 25/28; A61P 27/02; A61P 29/00; A61P 35/00; A61P 35/04; A61P 37/02; A61P 37/06; A61P 37/08; A61P 3/10; A61P 5/14
See application file for complete search history.

(56) References Cited

U.S. PATENT DOCUMENTS

| | | |
|---|---|---|
| 7,435,828 B2 | 10/2008 | Binkert et al. |
| 7,626,037 B2 | 12/2009 | Binkert et al. |
| 7,875,726 B2 | 1/2011 | Binkert et al. |
| 7,879,821 B2 | 2/2011 | Hauser et al. |
| 8,263,780 B2 | 9/2012 | Abele et al. |
| 8,273,779 B2 | 9/2012 | Binkert et al. |
| RE43,728 E | 10/2012 | Binkert et al. |
| RE43,833 E | 11/2012 | Binkert et al. |
| 8,492,441 B2 | 7/2013 | Legangneux |
| 8,524,752 B2 | 9/2013 | Binkert et al. |
| 8,785,484 B2 | 7/2014 | Brossard et al. |
| RE45,174 E | 9/2014 | Binkert et al. |
| 8,912,340 B2 | 12/2014 | Abele et al. |
| 9,000,018 B2 | 4/2015 | Binkert et al. |
| 9,062,014 B2 | 6/2015 | Bonham et al. |
| 9,340,518 B2 | 5/2016 | Herse et al. |
| 2010/0160259 A1 | 6/2010 | Schmouder et al. |
| 2011/0257133 A1 | 10/2011 | Schmouder et al. |
| 2014/0303217 A1 | 10/2014 | Brossard et al. |
| 2014/0315964 A1 | 10/2014 | Brossard et al. |
| 2014/0316140 A1 | 10/2014 | Brossard et al. |
| 2015/0265580 A1 | 9/2015 | Brossard et al. |
| 2019/0151292 A1 | 5/2019 | Dingemanse et al. |

FOREIGN PATENT DOCUMENTS

| | | |
|---|---|---|
| CN | 101980704 A | 2/2011 |
| JP | T-2005-535679 | 11/2005 |
| KR | 10-2427123 B1 | 7/2022 |
| WO | WO 2004/010987 | 2/2004 |
| WO | WO 2005/054215 | 6/2005 |
| WO | WO 2006/058316 | 6/2006 |
| WO | WO 2008/062376 | 5/2008 |
| WO | WO 2009/115954 | 9/2009 |
| WO | WO 2010/046835 | 4/2010 |
| WO | WO 2010/072703 | 7/2010 |
| WO | WO 2010/075239 | 7/2010 |
| WO | WO 2014/027330 | 2/2014 |
| WO | WO 2016/092042 | 6/2016 |

OTHER PUBLICATIONS

Olsson et al. (J Neurol Neurosurg Pschiatry, 2014, 85: 1198-1208). (Year: 2014).*
"Actelion's Orally Active Selective S1P1 Receptor Agonist to be Jointly Developed/ Promoted with Roche in Autoimmune Disorders and Transplantation; Deal Potentially Worth well over US$630 Million to Actelion", USCULO Elatal Report; Translating Research into Practice, p. 1, (2009).
Brinkmann, "Sphingosine 1-phosphate receptors in health and disease: Mechanistic insights from gene deletion studies and reverse pharmacology", Pharmacology & Therapeutics, vol. 115, p. 84-105, (2007).
Brossard et al., "Effects on heart rate of three different up-titration regimens of ponesimod, a selective S1P1 receptor modulator, and of re-initiation of treatment in healthy male and female subjects", ECTRIMS Lyon France, p. 468, (2012).
Brossard et al., "Effects of three different up-titration regimens of ponesimod, a selective S1P1 receptor agonist, on heart rate", ECTRIMS Lyon France, p. 109, (2012).
Brossard et al., "Ascending multiple-dose study with ponesimod, a selective S1P1 receptor agonist: tolerability, safety, pharmacokinetics, and pharmacodynamics", ECTRIMS Lyon France, p. 109, (2012).
Brossard et al., "Ascending single-dose study with ponesimod, a selective S1P1 receptor agonist: safety, pharmacokinetics, pharmacodynamics, and modeling", ECTRIMS Lyon France, p. 111, (2012).
Brossard et al., "Pharmacokinetics and pharmacodynamics of ponesimod, a selective S1P1 receptor modulator, in the first-in-human study", British Journal of Clinical Pharmacology, vol. 76(6), p. 888-896, (2013).
Brossard et al., "Effects on heart rate of three different up-titration regimens of ponesimod, a selective S1P1 receptor modulator, and of re-initiation of treatment in healthy male and female subjects", ECTRIMS Lyon France, (2012).

(Continued)

*Primary Examiner* — Umamaheswari Ramachandran
(74) *Attorney, Agent, or Firm* — BakerHostetler

(57) ABSTRACT

The present invention relates to a dosing regimen for (R)-5-[3-chloro-4-(2,3-dihydroxy-propoxy)-benz[Z]ylidene]-2-([Z]-propylimino)-3-o-tolyl-thiazolidin-4-one.

15 Claims, No Drawings

(56) References Cited

OTHER PUBLICATIONS

Brossard et al., "A randomised, double-blind, ascending multiple-dose study with ponesimod, a selective S1P1 receptor modulator: safety, pharmacokinetics, pharmacodynamics", ECTRIMS Lyon France, (2012).
Brossard et al., "Multiple-Dose Tolerability, Pharmacokinetics, and Pharmacodynamics of Ponesimod, an S1P1 Receptor Modulator: Favorable Impact of Dose Up-Titration", The Journal of Clinical Pharmacology, p. 1-10, (2013).
Brossard et al., "Pii-109; Effects of Three Different Up-Titration Regimens of Ponesimod, a Selective S1p1 Receptor Agonist, on Heart Rate", Nature, vol. 91, p. S92-S93, (2012).
Brossard et al., " Pii-110; Ascending Multiple-Dose Study With Ponesimod, a Selective S1p1 Receptor Agonist: Tolerability, Safety, Pharmacokinetics, and Pharmacodynamics", Nature, vol. 91, p. S93, (2012).
Brossard et al., "Pii-111; Ascending Single-Dose Study With Ponesimod, a Selective S1p1 Receptor Agonist: Safety, Pharmacokinetics, Pharmacodynamics, and Modeling", Nature, vol. 91, p. S93, (2012).
Bunemann et al., "Activation of Muscarinic K+ Current in Guinea-Pig Atrial Myocytes by sphingosine-1-phosphate", Journal of Physiology, vol. 489.3, p. 701-707, (1995).
Davidov et al., "Chronic nitric oxide synthase blockade desensitizes the heart to the negative metabolic effects of nitric oxide", Life Sciences, vol. 79, p. 1674-1680, (2006).
Frolkis et al., "The Role of Invertors (Intracellular Activators) in Age-Related Changes in Cell Response to Hormones", Experimental Gerontology, vol. 30(3/4), p. 401-414, (1995).
Fujishiro et al., "Use of Sphingosine-1-Phosphate 1 Receptor Agonist, KRP-203, in Combination with a Sub therapeutic Dose of Cyclosporine A for Rat Renal Transplantation", Transplantation, vol. 82(6), p. 804-812, (2006).
Guo et al., "Effects of Sphingosine 1-phosphate on pacemaker activity in rabbit sino-atrial node cells", European Journal of Physiology, vol. 438, p. 642-648, (1999).
Hale et al., "Selecting against S1P3 enhances the acute cardiovascular Tolerability of 3-(N-benzyl) aminopropylphosphonic acid S1P receptor agonists", Bioorganic & Medicinal Chemistry Letters, vol. 14, p. 3501-3505, (2004).
Himmel et al., "Evidence for Edg-3 Receptor-Mediated Activation of IK.ACh by Sphingosine-1-Phosphate in Human Atrial Cardiomyocytes", Molecular Pharmacology, vol. 58, p. 449-454, (2000).
Hoch et al., "Effect of Ponesimod, a Selective S1P1 Receptor Modulator, on the QT Interval in Healthy Individuals", Basic & Clinical Pharmacology & Toxicology, vol. 116, p. 429-437, (2015).
Hoch et al., "Oc015—Up-Titration Study With Ponesimod, a Selective S1p1 Receptor Modulator, to Assess its Maximum Tolerated Dose in Healthy Subjects", Clinical Therapeutics, vol. 35(8S), p. e6-e7, (2013).
Hoch et al., "The Proceedings of the 12th Conference of the European Association for Clinical Pharmacology and Therapeutics", Clinical Therapeutics, vol. XX(xx), (2015).
Hoch et al., "PP162—Thorough QT study with ponesimod, a selective S1P1 receptor modulator", Clinical Therapeutics, vol. 35(8S), p. e68-e69, (2013).
Hoch et al., "Thorough QT study with ponesimod, a selective S1P1 receptor modulator", EACPT Congress, p. pp. 162, (2013).
Hoch et al., "A novel gradual up-titration regimen mitigates the first-dose effects of ponesimod, a selective S1P1 receptor modulator", 12th European Association for Clinical Pharmacology and Therapeutics (EACPT) Congress, Madrid, Spain, (2015).
Hoch et al., "A Novel Gradual Up-Titration Regimen Mitigates the First—Dose Effects of Ponesimod, a Selective S1p1 Receptor Modulator", Clinical Therapeutics, vol. 37 (8S), e36e37, (2015).
Hoch et al., "Clinical pharmacology of ponesimod, a selective S1P1 receptor modulator, after uptitration to supratherapeutic doses in healthy subjects", European Journal of Pharmaceutical Sciences, vol. 63, p. 147-153, (2014).

Huwiler et al., "New players on the center stage: Sphingosine 1-phosphate and its receptors as drug targets", Biochemical Pharmacology, p. 1-8, (2008).
International Search Report of International Application No. PCT/EP2015/079208, dated Mar. 4, 2016, 4 pages.
Juif et al., "Mitigation of Initial Cardiodynamic Effects of the $S_1P_1$ Receptor Modulator Ponesimod Using a Novel Up-Titration Regimen", The Journal of Clinical Pharmacology, vol. 57(3), p. 401-410, (2017).
Kappos et al., "Siponimod ($BAF_{312}$) for the treatment of Secondary Progressive Multiple Sclerosis: Design of the Phase 3 Expand Trial", Multiple Sclerosis and Related Disorders, vol. 3(6), p. 752, (2014). (http://dx.doi.org/10.1016/j.msard.2014.09.185).
Keller et al., "Immunomodulator FTY720 Induces Myofibroblast Differentiation via the Lysophospholid Receptor S1P3 and Smad3 Signaling", The American Journal of Pathology, vol. 170, p. 281-292, (2007).
Kovarik et al., "A Mechanistic Study to Assess Whether Isoproterenol Can Reverse the Negative Chronotropic Effect of Fingolimod", Pharmacodynamics, p. 1-8, (2008).
Koyrakh et al., "The Heart Rate Decrease Caused by Acute FTY720 Administration is Mediated by the G-Protein-Gated Potassium Channel IKACH", American Journal of Transplantation, vol. 5, p. 529-536, (2005).
Krause et al., "Population modeling of the pharmacokinetics and pharmacodynamics of ponesimod, a selective S1P1 receptor agonist", University of Auckland, New Zealand, p. 78, (2012).
Krause et al., "Population modeling of the pharmacokinetics and pharmacodynamics of ponesimod, a selective S1P1 receptor agonist", Nature, vol. 91, p. S36-S37, (2012).
Krause et al., "Population pharmacokinetics and pharmacodynamics of ponesimod, a selective S1P1 receptor modulator", Journal of Pharmacokinetics Pharmacodynamics, vol. 41, p. 261-278, (2014).
Legangneux et al., "BAF312 Dose-Titration Scheme Significantly Attenuates Initial Heart Rate Reducing Effects in Healthy Subjects", 63rd American Academy of Neurology Annual Meeting, Honolulu Hawaii, (2011).
Legangneux et al., "BAF312 Dose-Titration Scheme Significantly Attenuates Initial Heart Rate Reducing Effects in Healthy Subjects", British Journal of Clinical Pharmacology, vol. 75(3), p. 831-841, (2012).
Lott et al., "Modeling Tolerance Development for the Effect on Heart Rate of the Selective $S1P_1$ Receptor Modulator Ponesimod," *Clinical Pharmacology & Therapeutics*, 10 pages (2017); DOI: 10.1002/cpt.877.
Lott et al., "Tolerance modeling: effects of the selective $S_1P_1$ receptor modulator ponesimod on heart rate", Universitat des Saarlandes—Population Approach Group Europe, $26^{th}$ Meeting, Budapest 2017, p. 1, (2017).
Ochi et al., "Sphingosine-1-phosphate Effects on Guinea Pig Atrial Myocytes: Alterations in Action Potentials and K+ Currents", Cardiovascular Research, vol. 70, p. 88-96, (2006).
Olsson et al., "Oral ponesimod in relapsing—remitting multiple sclerosis: a randomised phase II trial", J Neurol Neurosurg Psychiatry., vol. 85, p. 1198-1208, (2014).
Peters et al., "Sphingosine-1-phosphate signaling in the cardiovascular system", Current Opinion in Pharmacology, vol. 7, p. 1-7, (2007).
Remington, The Science and Practice of Pharmacy, 21st Edition, Part 5, Pharmaceutical Manufacturing; 2005.
Rey et al., "Desensitization by Progressive Up-Titration Prevents First-Dose Effects on the Heart: Guinea Pig Study with Ponesimod, a Selective S1P1 Receptor Modulator", PlosOne, vol. 8(9), p. e74285 (1-7), (2013).
Reyes et al., "Effects of ponesimod, a selective S1P1 receptor modulator, on the pharmacokinetics of a hormonal combination contraceptive", European Journal of Clinical Pharmacology, vol. 70, p. 287-293, (2014).
Sanna et al., "Sphingosine 1-Phosphate (SIP) Receptor Subtypes S1P1 and S1P3, Respectively, Regulate Lymphocyte Recirculation and Heart Rate*", The Journal of Biological Chemistry, vol. 279(4), p. 13839-13848, (2004).

(56) References Cited

OTHER PUBLICATIONS

Scherz et al., "Three Different Up-Titration Regimens of Ponesimod, an S1P1 Receptor Modulator, in Healthy Subjects", The Journal of Clinical Pharmacology, p. 1-10, (2015).

Schmouder et al., "FTY720: Placebo-Controlled Study of the Effect on Cardiac Rate and Rhythm in Healthy Subjects", Journal of Clinical Pharmacology, vol. 46, p. 895-904, (2006).

Stahl et al., "Handbook of Pharmaceuticals Salts: Properties, Selection, and use", International Union of Pure and Applied Chemistry, p. 329-350, (2008).

Vaclavkova et al., "Oral ponesimod in patients with chronic plaque psoriasis: a randomised, double-blind, placebo-controlled phase 2 trial", The Lancet, p. 1-10, (2014).

Wouters et al., "Pharmaceutical Salts and Cocrystals", RSC Drug Discovery, p. 1-10, (2012).

Fernández et al., "Review of the Novelties Presented at the 28th Congress of the European Committee for Treatment and Research in Multiple Sclerosis (ECTRIMS) (III)," Rev Neurol., vol. 57, No. 7, pp. 317-329, (2013).

Piali et al., "The Selective Sphingosine 1-Phosphate Receptor 1 Agonist Ponesimod Protects against Lymphocyte-Mediated Tissue Inflammation," The Journal of Pharmacology and Experimental Therapeutics, vol. 337, No. 2, pp. 547-556, (2011).

Basile, "Titration of β-blockers in Heart Failure," Postgraduate Medicine, vol. 113, No. 3, p. 63-70, (2003).

Brossard et al., "Effects on Heart Rate of Three Different Up-titration Regimens of Ponesimod, A Selective S1P1 Receptor Modulator, and of Re-Initiation of Treatment in Healthy Male and Female Subjects," Multiple Sclerosis Journal, vol. 18, No. S4, p. 192, Abstract P468, 2 pages, (2012).

De Vries et al., "Guide to Good Prescribing: A Practical Manual," WHO Action Programme on Essential Drugs, 11 pages, (1994).

McCormack et al., "Is Bigger Better? An Argument for Very Low Starting Doses," CMAJ, vol. 183, No. 1, p. 65-69, (2011).

* cited by examiner

DOSING REGIMEN FOR A SELECTIVE S1P$_1$ RECEPTOR AGONIST

CROSS REFERENCE TO RELATED APPLICATIONS

This application is a divisional application of U.S. application Ser. No. 16/261,327, filed on Jan. 29, 2019, which is a divisional application of U.S. application Ser. No. 15/534,929, filed on Jun. 9, 2017, which claims the benefit of United States Application under 35 U.S.C. 371 of PCT Application No. PCT/EP2015/079208, filed on Dec. 10, 2015, which claims the benefit and priority to PCT Application No. PCT/EP2015/058202, filed on Apr. 15, 2015 and PCT Application No. PCT/EP2014/077469, filed on Dec. 11, 2014, the contents of each of which are incorporated herein by reference.

FIELD OF THE INVENTION

The present invention relates to a dosing regimen for (R)-5-[3-chloro-4-(2,3-dihydroxy-propoxy)-benz[Z]ylidene]-2-([Z]-propylimino)-3-o-tolyl-thiazolidin-4-one (hereinafter also referred to as "Compound 1").

DESCRIPTION OF THE INVENTION

The present invention provides a dosing regimen for Compound 1, by which adverse effects are minimized in subjects/patients during initiation of treatment, or upon re-initiation of treatment after drug discontinuation.

Compound 1 is a selective S1P$_1$ receptor agonist and oral administration thereof results in a consistent, sustained, and dose-dependent reduction in the number of peripheral blood lymphocytes. Compound 1 has been described to be useful in the treatment and/or prevention of diseases or disorders associated with an activated immune system (see e.g., WO 2005/054215 and WO 2009/115954). In particular, Compound 1 (INN: ponesimod) has shown clinical benefit in phase II trials in patients with moderate to severe chronic plaque psoriasis and in patients with relapsing-remitting multiple sclerosis (Olsson T. et al., Oral ponesimod in relapsing-remitting multiple sclerosis: a randomised phase II trial. *J Neurol Neurosurg Psychiatry*. 2014; 85 (11): 1198-1208; and Vaclavkova A. et al., Oral ponesimod in patients with chronic plaque psoriasis: a randomised, double-blind, placebo-controlled phase 2 trial. *Lancet*. 2014; 384 (9959): 2036-2045). Compound 1 may be prepared according to any procedure as disclosed in WO 2005/054215, WO 2008/062376, and WO 2014/027330.

WO 2010/046835 discloses different crystalline forms of Compound 1; it is to be understood that the present invention encompasses Compound 1 in any form including amorphous as well as crystalline forms of Compound 1. It is further to be understood that crystalline forms of Compound 1 encompasses all types of crystalline forms of Compound 1 including polymorphs of the mere molecule, solvates and hydrates, molecular salts and co-crystals (when the same molecule can be co-crystallized with different co-crystal formers) provided they are suitable for pharmaceutical administration. In a preferred embodiment, Compound 1 is in crystalline form A or C as described in WO 2010/046835. In a most preferred embodiment, Compound 1 is in crystalline form C.

Repeated daily oral dosing of 5 mg or more of Compound 1 to humans results in a consistent, sustained, and dose-dependent reduction in the number of peripheral blood lymphocytes. It has been surprisingly found, however, that the selective S1P$_1$ receptor agonist Compound 1 transiently reduces heart rate in humans, with maximal effects 1-3 hours after administration. In some individuals this is accompanied by similarly transient increases in the PR interval in the electrocardiogram (ECG), and an associated irregular heart rhythm (so-called Wenckebach rhythm). Occasional fatigue or dizziness also occur in the post-dose period. All of these effects wane with repeated dosing. The acute effects on e.g. heart rate, atrioventricular conduction, or fatigue and dizziness are undesirable, and methods to minimize these effects would be valuable for maximizing the tolerability and safety of Compound 1 and minimizing associated monitoring requirements in the early phase of dosing initiation, or, after a drug interruption, at re-initiation of drug therapy.

The subject matter of the present invention therefore provides a dosing regimen for Compound 1 which minimizes the incidence or severity of adverse effects during initiation of treatment or upon re-initiation of treatment after drug discontinuation. WO 2009/115954 disceses a dosing regimen for selective S1P$_1$ receptor agonists such as for example Compound 1. In clinical phase II studies, Compound 1 was administered according to a dosing regimen herein after also referred to as regimen B which consisted of a once daily oral administration of Compound 1 at a dose of 10 mg for 7 days followed by 20 mg on day 8 (Olsson T. et al., Oral ponesimod in relapsing-remitting multiple sclerosis: a randomised phase II trial. *J Neurol Neurosurg Psychiatry*. 2014; 85 (11): 1198-1208; and Vaclavkova A. et al., Oral ponesimod in patients with chronic plaque psoriasis: a randomised, double-blind, placebo-controlled phase 2 trial. *Lancet*. 2014; 384 (9959): 2036-2045). However, the dosing regimen of the present invention exhibits advantages compared to dosing regimen B (see Experimental Part below). Using the novel up-titration regimen according to the present invention, the cardiodynamic first-dose and subsequent effects and the safety and tolerability of Compound 1 are mitigated compared to the previous up-titration regimen.

i) In particular, the present invention relates to Compound 1, or a pharmaceutically acceptable salt thereof, for use in the treatment of a disease or disorder associated with an activated immune system, wherein during initiation of treatment, or upon re-initiation of treatment after drug discontinuation, Compound 1, or a pharmaceutically acceptable salt thereof, is to be administered to a human subject orally once daily as follows: 2 mg of Compound 1 on days 1 and 2; 3 mg of Compound 1 on days 3 and 4; 4 mg of Compound 1 on days 5 and 6; 5 mg of Compound 1 on day 7; 6 mg of Compound 1 on day 8; 7 mg of Compound 1 on day 9; 8 mg of Compound 1 on day 10; and 9 mg of Compound 1 on day 11; followed by (a) the maintenance dose of 10 mg of Compound 1 to be administered orally once daily from day 12 onwards; or (b) 10 mg of Compound 1 to be administered orally once daily for 2, 3 or 4 days (i.e., on days 12 and 13; days 12, 13, and 14; or days 12, 13, 14, and 15), especially for 3 days (i.e., on days 12, 13, and 14), followed by the maintenance dose of 20 mg of Compound 1 to be administered orally once daily (i.e., from the day following the day of the last administration of the 10 mg dose onwards).

For clarity reasons it is noted that the once daily oral doses referred to in the above embodiment i) refer to the amount of Compound 1 in its free form. In case that for example a pharmaceutically acceptable salt of Compound 1 is used, the amounts given above will need to be adapted accordingly. In a preferred embodiment of the present invention Compound 1 is administered in its free form.

The above sub-embodiment i) (b), i.e. the up-titration of Compound 1 to the maintenance dose of 20 mg p.o. once daily, is preferred, especially in case Compound 1 is administered as monotherapy and especially in case of monotherapy for the treatment of multiple sclerosis. However, it is to be understood that the dosing regimen according to sub-embodiment i) (b) does not exclude that the maintenance dose of 20 mg p.o. once daily is later lowered, to e.g. 10 mg p.o. once daily, for e.g. safety reasons if, for example, the number of peripheral blood lymphocytes falls below a critical limit.

The production of oral pharmaceutical compositions of Compound 1 can be effected in a manner which will be familiar to any person skilled in the art (see for example Remington, *The Science and Practice of Pharmacy*, 21st Edition (2005), Part 5, "Pharmaceutical Manufacturing" [published by Lippincott Williams & Wilkins]) by bringing Compound 1 or a pharmaceutically acceptable salt thereof into a galenical administration form together with suitable, non-toxic, inert, pharmaceutically acceptable solid or liquid carrier materials and, if desired, usual pharmaceutical adjuvants.

ii) A further embodiment of the invention relates to Compound 1, or a pharmaceutically acceptable salt thereof, for use according to embodiment i), wherein Compound 1, or a pharmaceutically acceptable salt thereof, is to be administered to a human subject orally once daily as follows: 2 mg of Compound 1 on days 1 and 2; 3 mg of Compound 1 on days 3 and 4; 4 mg of Compound 1 on days 5 and 6; 5 mg of Compound 1 on day 7; 6 mg of Compound 1 on day 8; 7 mg of Compound 1 on day 9; 8 mg of Compound 1 on day 10; and 9 mg of Compound 1 on day 11; followed by 10 mg of Compound 1 to be administered orally once daily for 2, 3 or 4 days, especially for 3 days; followed by the maintenance dose of 20 mg of Compound 1 to be administered orally once daily.

iii) A further embodiment of the invention relates to Compound 1, or a pharmaceutically acceptable salt thereof, for use according to embodiment i), wherein Compound 1, or a pharmaceutically acceptable salt thereof, is to be administered to a human subject orally once daily as follows: 2 mg of Compound 1 on days 1 and 2; 3 mg of Compound 1 on days 3 and 4; 4 mg of Compound 1 on days 5 and 6; 5 mg of Compound 1 on day 7; 6 mg of Compound 1 on day 8; 7 mg of Compound 1 on day 9; 8 mg of Compound 1 on day 10; and 9 mg of Compound 1 on day 11; followed by 10 mg of Compound 1 to be administered orally once daily on days 12, 13, and 14; followed by the maintenance dose of 20 mg of Compound 1 to be administered orally once daily from day 15 onwards.

iv) A further embodiment of the invention relates to Compound 1, or a pharmaceutically acceptable salt thereof, for use according to embodiment i), wherein Compound 1, or a pharmaceutically acceptable salt thereof, is to be administered to a human subject orally once daily as follows: 2 mg of Compound 1 on days 1 and 2; 3 mg of Compound 1 on days 3 and 4; 4 mg of Compound 1 on days 5 and 6; 5 mg of Compound 1 on day 7; 6 mg of Compound 1 on day 8; 7 mg of Compound 1 on day 9; 8 mg of Compound 1 on day 10; and 9 mg of Compound 1 on day 11; followed by the maintenance dose of 10 mg of Compound 1 to be administered orally once daily from day 12 onwards.

v) A further embodiment of the invention relates to Compound 1, or a pharmaceutically acceptable salt thereof, for use according to any one of embodiments i) to iv), wherein the disease or disorder to be treated is selected from the group consisting of rejection of transplanted organs such as kidney, liver, heart, lung, pancreas, cornea, and skin; graft-versus-host disease; autoimmune syndromes including rheumatoid arthritis, multiple sclerosis, inflammatory bowel diseases such as Crohn's disease and ulcerative colitis, psoriasis, psoriatic arthritis, thyroiditis such as Hashimoto's thyroiditis, and uveo-retinitis; atopic diseases such as rhinitis, conjunctivitis, and dermatitis; asthma; type I diabetes; post-infectious autoimmune diseases including rheumatic fever and post-infectious glomerulonephritis; solid cancers; and tumor metastasis.

vi) A further embodiment of the invention relates to Compound 1, or a pharmaceutically acceptable salt thereof, for use according to any one of embodiments i) to iv), wherein the disease or disorder to be treated is selected from the group consisting of rejection of transplanted organs selected from kidney, liver, heart and lung; graft-versus-host disease; autoimmune syndromes selected from rheumatoid arthritis, multiple sclerosis, psoriasis, psoriatic arthritis, Crohn's disease, and Hashimoto's thyroiditis; and atopic dermatitis.

vii) A further embodiment of the invention relates to Compound 1, or a pharmaceutically acceptable salt thereof, for use according to any one of embodiments i) to iv), wherein the disease or disorder to be treated is graft-versus-host disease.

viii) A further embodiment of the invention relates to Compound 1, or a pharmaceutically acceptable salt thereof, for use according to any one of embodiments i) to iv), wherein the disease or disorder to be treated is chronic graft-versus-host disease.

ix) A further embodiment of the invention relates to Compound 1, or a pharmaceutically acceptable salt thereof, for use according to any one of embodiments i) to iv), wherein the disease or disorder to be treated is multiple sclerosis.

x) A further embodiment of the invention relates to Compound 1, or a pharmaceutically acceptable salt thereof, for use according to any one of embodiments i) to iv), wherein the disease or disorder to be treated is relapsing multiple sclerosis.

xi) A further embodiment of the invention relates to Compound 1, or a pharmaceutically acceptable salt thereof, for use according to any one of embodiments i) to iv), wherein the disease or disorder to be treated is relapsing-remitting multiple sclerosis.

Based on the dependencies of the different embodiments as disclosed hereinabove, the following embodiments are thus possible and intended and herewith specifically disclosed in individualized form: i), ii)+i), iii)+i), iv)+i), v)+i), v)+ii)+i), v)+iii)+i), v)+iv)+i), vi)+i), vi)+ii)+i), vi)+iii)+i), vi)+iv)+i), vii)+i), vii)+ii)+i), vii)+iii)+i), vii)+iv)+i), viii)+i), viii)+ii)+i), viii)+iii)+i), viii)+iv)+i), ix)+i), ix)+ii)+i), ix)+iii)+i), ix)+iv)+i), x)+i), x)+ii)+i), x)+iii)+i), x)+iv)+i), xi)+i), xi)+ii)+i), xi)+iii)+i), and xi)+iv)+i).

In the list above, the numbers refer to the embodiments according to their numbering provided hereinabove whereas "+" indicates the dependency from another embodiment. The different individualized embodiments are separated by commas. In other words, "viii)+iii)+i)" for example refers to embodiment viii) depending on embodiment iii) depending on embodiment i), i.e. embodiment "viii)+iii)+i)" corresponds to the dosing regimen of embodiment i) further limited by the features of the embodiments iii) and viii).

The present invention also relates to a method of reducing the number of peripheral blood lymphocytes in a human subject in need thereof, wherein during initiation of treatment, or upon re-initiation of treatment after drug discontinuation, Compound 1, or a pharmaceutically acceptable salt thereof, is administered to the human subject orally once daily as described in any one of above embodiments i) to iv).

The general terms and expressions used hereinbefore and/or hereinafter preferably have, within this disclosure, the following meanings:

The term "pharmaceutically acceptable salt" refers to salts that retain the desired biological activity of the subject compound and exhibit minimal undesired toxicological effects. Such salts include inorganic or organic acid and/or base addition salts depending on the presence of basic and/or acidic groups in the subject compound. For reference see for example 'Handbook of Pharmaceutical Salts. Properties, Selection and Use.', P. Heinrich Stahl, Camille G. Wermuth (Eds.), Wiley-VCH, 2008 and 'Pharmaceutical Salts and Co-crystals', Johan Wouters and Luc Quéré (Eds.), RSC Publishing, 2012.

The expression "upon re-initiation of treatment after drug discontinuation" means an interruption of the administration of Compound 1, or a pharmaceutically acceptable salt thereof, of at least one, at least two or preferably at least 3 days before treatment is re-initiated.

The term "p.o." means oral administration.

For the sake of clarity, relapsing multiple sclerosis means relapsing forms of multiple sclerosis which includes forms of multiple sclerosis with relapses. Examples of relapsing multiple sclerosis are relapsing-remitting multiple sclerosis, secondary progressive multiple sclerosis with relapses, and progressive relapsing multiple sclerosis.

Experimental Part

In a single-center, double-blind, placebo-controlled, randomized, two-way cross-over study, 32 healthy subjects (15 males) received placebo on Day 1 followed by multiple-dose administration of either ponesimod or placebo (ratio 3:1). Ponesimod was administered alternately using regimen A (incremental dose increase from 2 to 20 mg) or B (10 mg for 7 days followed by a single-dose administration of 20 mg). Cardiodynamic (Holter and 12-lead ECG), pharmacokinetic, pharmacodynamic (total lymphocyte count), and safety variables were assessed.

Subjects

In this trial, 32 healthy male and female subjects (15 and 17, respectively; mean±standard deviation [SD] body weight was 73.4±11.5 kg) aged between 18 and 57 years (34±12.7 years) were enrolled and received ponesimod or its matching placebo (3:1 ratio active:placebo). The health of the subjects was assessed at the screening visit, which included recording of the medical history, medications taken during the 3 months preceding the screening visit, a physical examination, measurement of body weight and height, clinical laboratory tests, recording of vital signs, and standard ECG. At screening and prior to first dosing, subjects had to have PR interval <200 ms, heart rate (HR) >50 beats per minute (bpm), systolic (SBP) and diastolic (DBP) blood pressure 90-145 and 50-90 mmHg, respectively, 24-h Holter ECG without clinically relevant abnormalities, forced expiratory volume in 1 second ($FEV_1$) and forced vital capacity (FVC) >80% of the predicted value and $FEV_1/FVC$>70%, and a normal total lymphocyte count (>1000 total lymphocyte count/μL). Women of childbearing potential had to use two reliable methods of contraception and should not be pregnant or lactating.

Study Design

The enrolled subjects came to the study center for each treatment period on Day −2 and participated in a run-in (all study procedures performed without study drug administration) on Day −1. On Day 1, subjects were randomized to one of the two possible sequences of the two up-titration regimens A and B (ratio 1:1). On Day 1, all subjects received placebo; the first study drug administration (or its matching placebo) occurred on Day 2. Regimen A consisted of the novel up-titration regimen: ponesimod was administered once daily (o.d.) orally at a dose of 2 mg on Day 2 and Day 3, 3 mg on Day 4 and Day 5, 4 mg on Day 6 and Day 7, 5 mg on Day 8, 6 mg on Day 9, 7 mg on Day 10, 8 mg on Day 11, 9 mg on Day 12, 10 mg on Day 13 and Day 14, and 20 mg on Day 15. The reference regimen (regimen B) was based on previous studies (Olsson T. et al., Oral ponesimod in relapsing-remitting multiple sclerosis: a randomised phase II trial. *J Neurol Neurosurg Psychiatry.* 2014; 85 (11): 1198-1208; and Vaclavkova A. et al., Oral ponesimod in patients with chronic plaque psoriasis: a randomised, double-blind, placebo-controlled phase 2 trial. *Lancet.* 2014; 384 (9959): 2036-2045) and consisted of an o.d. oral administration of ponesimod at a dose of 10 mg for 7 days (i.e., from Day 2 to Day 8) and 20 mg on Day 9. From Day 10 to Day 15 subjects received o.d. the matching placebo. In the placebo group (1:1 sex ratio), subjects received placebo from Day 1 to Day 15. All treatments were administered at the same time in the morning (fasted condition) with approximately 240 mL of water.

The subjects remained in the clinic until at least the morning of Day 16 of each treatment period. Subjects were discharged if HR was >45 bpm and >70% of the HR at baseline without any clinically relevant ECG abnormalities. There was a washout period of 12 to 14 days between the last study drug administration (i.e., Day 15) in the first treatment period and the first study drug administration in the second treatment period. Subjects came back to the clinic 5-7 days after last study drug administration at the end of each treatment period for the end-of-first period (EOFP) visit and the end-of-study (EOS) visit.

Cardiodynamic Assessments

Cardiodynamic endpoints were assessed using Holter and 12-lead ECG. The 24-h Holter recordings were performed on Day −1, Day 1, Day 2, Day 9, Day 13, and Day 15. The 12-h Holter recordings were performed on the other days. In addition, Holter data were used to estimate the area under the effect curve (AUEC) for HR. 12-lead ECGs were performed from Day −1 to Day 16 at pre-dose and 1, 2, 3, 4, 5, 6, 8, 10, and 12 h after study drug administration. An additional 12-lead ECG recording was performed at EOFP and EOS. Heart rate nadir, $E_{max}$ (maximum decrease of mean hourly HR from baseline, which was defined as the mean of the time-matched assessments measured on Day −1 and Day 1 pre-dose), and occurrence of values of interest (HR <45 bpm, HR decrease from baseline >20 bpm, and PR interval increase from baseline >20 ms), and AV-blocks (i.e., PR interval >210 ms) were obtained with 12-lead ECG.

Safety and Tolerability

Safety and tolerability were evaluated by monitoring adverse events (AEs), vital signs measurements (supine blood pressure), pulmonary function tests (PFTs; i.e., $FEV_1$ and FVC), clinical laboratory, physical, and neurological examinations. Recording of blood pressure was performed at the same time-points as 12-lead ECG.

Pharmacokinetic and Pharmacodynamic Assessments

Blood samples of about 3 mL were collected in ethylene di-amine tetra acetic acid tubes at pre-dose and 3 h after study drug administration from Day 1 to Day 15 in each treatment period. After centrifugation, plasma was transferred into a polypropylene tube and stored at −21° C. (±5° C.) pending analysis. Plasma concentrations of ponesimod were determined using a validated liquid chromatography coupled to tandem mass spectrometry assay with a lower limit of quantification of 1 ng/mL (Brossard P. et al., Pharmacokinetics and pharmacodynamics of ponesimod, a selective $S1P_1$ receptor modulator, in the first-in-human study. *British journal of clinical pharmacology*. 2013; 76 (6): 888-896). Trough samples were taken on Day −1, Day 3, Day 6, Day 9, Day 12, and Day 15 of each treatment period and at EOFP and EOS to assess total lymphocyte count by hemocytometry.

Statistical Analysis

Cardiodynamic and pharmacodynamic data are expressed as mean±SD. Repeated measure one-way ANOVAs followed by Tukey's multiple-comparisons tests were used to perform inter-group (i.e., placebo vs. regimen A vs. regimen B) comparisons. Student's t-tests were employed to perform intra-group (baseline vs. treatment) comparisons. Differences were considered to be statistically significant at p<0.05. SAS® version 9.2 (SAS Institute, Cary, N.C., USA) was used for the statistical analysis and descriptive statistics of clinical data.

Results

Cardiodynamic Endpoints

There was no relevant difference in mean hourly HR (Holter ECG) between Day −1 (run-in) and Day 1 (all subjects treated with placebo). On Day 1, the placebo effect on mean hourly HR was similar between each treatment period. The first dose of ponesimod (Day 2) triggered a decrease in mean hourly HR from baseline. This effect was limited in subjects treated with placebo for whom the mean maximum decrease (±SD) was observed 2 h post-dose (0±5.2 bpm, p>0.05 vs. baseline [baseline defined as the mean of the pre-dose assessments on Day −1 and Day 1]). The mean hourly HR reduction was more pronounced following ponesimod administration and the nadir was observed 2 h (−6±7.4 bpm, p<0.05 vs. baseline) and 3 h (−12±6.9 bpm, p<0.05 vs. baseline) following administration of ponesimod in regimen A and regimen B, respectively. The mean hourly HR returned to pre-dose values 4-5 h after administration. This effect was again observed on Day 3 (2 h post-dose) with placebo (−2±4.9 bpm, p>0.05 vs. baseline), regimen A (−8±5.3 bpm, p<0.05 vs. baseline), and regimen B (−9±5.7 bpm, p<0.05 vs. baseline). From Day 4 to the last day of treatment, no further significant decreases were observed in mean hourly HR following ponesimod administration. Assessments on Day 2 and Day 3 showed that the HR nadir value was lower following administration of ponesimod with regimen B than regimen A (p<0.05) and placebo (p<0.05).

On Day 1, when all subjects received placebo, similar mean AUEC from 0 to 12 h after dosing ($AUEC_{0-12}$) values were calculated in the different treatment groups (placebo: −33.3±32.7, treatment regimen A: −11.8±34.4, and treatment regimen B: −26.4±37.0 bpm·h). On Day 2, the first administration of ponesimod led to a decrease in HR that was reflected by a lower mean $AUEC_{0-12}$ in both treatment regimen A (−70.7±38.7 bpm·h) and treatment regimen B (−128.6±63.3 bpm·h) than in the placebo group (−5.3±36.8 bpm·h, p<0.05 placebo vs. ponesimod). After the first administration, AUEC was significantly greater (i.e., lesser effect) following the up-titration regimen A compared to treatment regimen B (p<0.05). On Day 3, the mean $AUEC_{0-12}$ was still greater following treatment regimen A (−105.5±49.0 bpm·h) than following ponesimod 10 mg (−146.6±59.8 bpm·h, p<0.05).

These Holter data were supported by 12-lead ECG data. On Day 1, multiple comparisons revealed that HR profiles were similar during the day: a slight decrease during the first 2 h after administration (~−2.7 bpm) followed by an increase (~12 bpm, 5 h after placebo administration). On Day 2, following ponesimod at a dose of 2 mg (regimen A) and 10 mg (regimen B), a significant decrease was observed 2 h post-dose and the mean maximum change from baseline (baseline defined as the mean of the pre-dose assessments on Day −1 and Day 1) was −9±5.3 bpm (p<0.05) and −13±6.2 bpm (p<0.05), respectively. The first-dose effect on HR reduction was greater following regimen B compared to placebo (−4 ±7.6 bpm, 2 h post-dose, p<0.05 vs. baseline) or regimen A (p<0.05). HR returned to baseline values within 3 and 4 h post-dose following treatment regimen A and regimen B, respectively. On Day 3, a decrease in HR was observed 2 h after administration of the second dose of ponesimod at a dose of 2 mg (−9±5.2 bpm vs. baseline) or 10 mg (−10±5.1 bpm vs. baseline). This decrease was more pronounced when compared to placebo (nadir: −4±4.7 bpm, p<0.05 vs. baseline). These differences were supported by the $E_{max}$ values. From Day 4 to the last day of administration of ponesimod (i.e., Day 15 for regimen A and Day 9 for regimen B), the pre-dose HR values were slightly lower in ponesimod-treated subjects (range: 56-60 bpm) compared to subjects who received placebo (range 60-64 bpm) but the HR-time profile was similar.

The occurrence of HR <45 bpm (at any time during the regimen from 12-lead ECG) was more pronounced in regimen B (58 events in 4 subjects) compared to regimen A (20 events in 3 subjects). There were no subjects who experienced HR <45 bpm in the placebo group.

During the course of the study, occurrence of PR interval >210 ms was lower following placebo (33 events in 4 subjects) than regimen A (79 events in 6 subjects) and regimen B (143 events in 8 subjects).

The occurrence of HR <45 bpm, HR decrease from baseline (baseline defined as the mean of the pre-dose assessments on Day −1 and Day 1) >20 bpm, PR interval 200 ms, or PR interval increase from baseline (baseline defined as the mean of the pre-dose assessments on Day −1 and Day 1) >20 ms during the first 12 hours on Day 2 and the percentage of subjects experiencing at least one of these events was similar between placebo (15 events in 5 subjects, i.e., 31.3% of the subjects) and regimen A (14 events in 6 subjects, i.e., 25% of the subjects). The number of events and subjects displaying at least one event was higher in regimen B (43 events in 12 subjects, i.e., 50% of the subjects).

Analysis of 12-lead ECG abnormalities revealed that sinus bradycardia occurred more often following regimen B compared to regimen A (Table 1). Events of AV-block first degree, AV-block second degree, and QT prolonged were only reported following placebo and regimen B (Table 1).

TABLE 1

Overall incidence of 12-lead ECG abnormalities

|  | Regimen A (N = 24)[#] | Regimen B (N = 24)[#] | Placebo (N = 16[†])[#] |
|---|---|---|---|
| Atrial rhythm | 4 (16.7)/19 | 2 (8.3)/12 | 5 (31.3)/7 |
| Supraventricular extrasystoles | 3 (12.5)/15 | 7 (29.2)/29 | 2 (12.5)/19 |
| Sinus bradycardia | 3 (12.5)/3 | 3 (12.5)/33 | — |
| Ventricular extrasystoles | 1 (4.2)/1 | 3 (12.5)/3 | 3 (18.8)/21 |
| Short PQ | — | 6 (25.0)/147 | 1 (6.3)/1 |
| QT prolonged | — | 6 (25.0)/142 | 7 (43.8)/21 |
| AV-block 1st degree | — | 6 (25.0)/130 | 4 (25.0)/27 |
| AV-block 2nd degree Mobitz I | — | 1 (4.2)/1 | 1 (6.3)/1 |
| Sinus arrhythmia | — | 12 (50.0)/98 | 15 (93.8)/266 |
| Atrial fibrillation | — | 1 (4.2)/1* | — |
| Sinus tachycardia | — | — | 2 (12.5)/4 |
| Supraventricular rhythm | — | — | 1 (6.3)/1 |

*Serious adverse event
[#]From Day 2 to EOFP or EOS visit
[†]Two treatment periods pooled
Data are presented as number of subjects (percentage)/number of events.

Safety and Tolerability

The total number of AEs and intensity of these AEs were similar across the different treatment groups. All AEs were of mild to moderate intensity. The most commonly reported AEs on ponesimod were headache, dizziness, and procedural site reaction, and these AEs were also among the most commonly reported by subjects in the placebo group. AEs of special interest related to cardiac function such as sinus bradycardia and palpitations were reported more frequently during regimen B compared to regimen A. One serious AE of atrial fibrillation was reported 6 h after administration of 20 mg ponesimod (regimen B). This event resolved without sequelae within 24 h.

Vital Signs, PFTs, and Clinical Laboratory Evaluation

No differences were observed in blood pressure (BP) between Day −1 and Day 1 (placebo) for any treatment regimen. A decrease in SBP and DBP was observed following the first administration of ponesimod with regimen A (SBP: −4±4.4 and DBP: −7±5.3 mmHg) and regimen B (SBP: −5±7.7 and DBP: −10±4.4 mmHg). The decreases in SBP and DBP were similar as those following placebo (SBP: −7±12.5 and DBP: −6±5.7 mmHg). On Day 1 (placebo), Day 2 (first administration of ponesimod) and along the course of the study, a similar number of subjects reported at least one event of SBP <90 mmHg. A decrease from baseline in SBP >20 mmHg occurred less often following ponesimod administered with treatment regimen A compared to treatment regimen B and placebo. Both number of events and subjects who experienced DBP <50 mmHg or decrease in DBP from baseline >15 mmHg were much more pronounced in the ponesimod-treated groups compared to placebo.

No treatment effect was observed on PFT variables and hematology variables (hemoglobin, hematocrit, red blood cell count, basophils, eosinophils, neutrophils, monocytes, and platelet count) although some out-of range values were reported for most subjects but none were considered as clinically significant.

Pharmacokinetic and Pharmacodynamic Endpoints

Using the up-titration regimen A, trough and 3 h post-dose plasma concentrations steadily increased. Similar concentrations were reached in regimen A at 3 h after the second dose of 10 mg ponesimod (i.e., Day 14) and the 5$^{th}$ dose of 10 mg ponesimod in regimen B (Day 6). Visual inspection revealed that the 10 mg steady-state conditions with regimen B were attained on Day 6. Plasma concentration 3 h after 20 mg of ponesimod was similar in regimen A (Day 15: 144.0±36.9 ng/mL) and regimen B (Day 9: 144.0±41.9 ng/mL).

As expected by its mode of action, a decrease of circulating total lymphocyte count was observed after ponesimod initiation. In regimen A, the decrease was more gradual when compared to regimen B. On Day 3, the mean percentage change from baseline (±SD) was greater with regimen B (−28.9±12.2%) than with regimen A (−11.6±10.2%, p<0.05) and placebo (−0.3±22.2%, p<0.05). On Day 6, the decrease from baseline in total lymphocyte count was more pronounced with either regimen A (−15.0±14.4%) or regimen B (−46.5±12.3%) than with placebo (−0.2±11.3%). Following the last dose of 10 mg ponesimod, a similar decrease in total lymphocyte count was observed with regimen A (Day 15 [before administration of the dose of 20 mg], −50.8±12.1%) and regimen B (Day 9 [before administration of the dose of 20 mg], −52.3±11.0%). Each individual total lymphocyte count returned to within the normal range (i.e., 80% of baseline) at EOFP and EOS.

The invention claimed is:

1. A method of administering (R)-5[3-chloro-4-(2,3-dihydroxy-propoxy)-benz[Z]ylidene]-2-([Z]-propylimino)-3-o-tolyl-thiazolidin-4-one (Compound 1), or a pharmaceutically acceptable salt thereof, to a subject in need thereof, for use in the treatment of a disease or disorder "selected from the group consisting of rejection of transplanted organs selected from kidney, liver, heart and lung; autoimmune syndromes selected from rheumatoid arthritis, psoriasis, psoriatic arthritis, Crohn's disease, and Hashimoto's thyroiditis; and atopic dermatitis" comprising the following steps: during initiation of treatment, or upon re-initiation of treatment after drug discontinuation, administering Compound 1, or a pharmaceutically acceptable salt thereof, orally once daily as follows: 2 mg of Compound 1 on days 1 and 2; 3 mg of Compound 1 on days 3 and 4; 4 mg of Compound 1 on days 5 and 6; 5 mg of Compound 1 on day 7; 6 mg of Compound 1 on day 8; 7 mg of Compound 1 on day 9; 8 mg of Compound 1 on day 10; and 9 mg of Compound 1 on day 11; followed by (a) administering the maintenance dose of 10 mg of Compound 1 orally once daily from day 12 onwards; or (b) administering 10 mg of Compound 1 orally once daily for 2, 3 or 4 days, followed by the maintenance dose of 20 mg of Compound 1 to be administered orally once daily.

2. The method of in claim 1, comprising administering Compound 1, or a pharmaceutically acceptable salt thereof, orally once daily as follows: 2 mg of Compound 1 on days 1 and 2; 3 mg of Compound 1 on days 3 and 4; 4 mg of Compound 1 on days 5 and 6; 5 mg of Compound 1 on day 7; 6 mg of Compound 1 on day 8; 7 mg of Compound 1 on day 9; 8 mg of Compound 1 on day 10; and 9 mg of Compound 1 on day 11; followed by administering 10 mg of Compound 1 to be administered orally once daily for 2, 3 or 4 days; followed by administering the maintenance dose of 20 mg of Compound 1 orally once daily.

3. The method of in claim 1, comprising administering Compound 1, or a pharmaceutically acceptable salt thereof, orally once daily as follows: 2 mg of Compound 1 on days 1 and 2; 3 mg of Compound 1 on days 3 and 4; 4 mg of Compound 1 on days 5 and 6; 5 mg of Compound 1 on day 7; 6 mg of Compound 1 on day 8; 7 mg of Compound 1 on day 9; 8 mg of Compound 1 on day 10; and 9 mg of Compound 1 on day 11; followed by administering 10 mg of Compound 1 orally once daily on days 12, 13, and 14; followed by administering the maintenance dose of 20 mg of Compound 1 orally once daily from day 15 onwards.

4. The method of in claim 1, comprising administering Compound 1, or a pharmaceutically acceptable salt thereof, is to be administered to a human subject orally once daily as follows: 2 mg of Compound 1 on days 1 and 2; 3 mg of Compound 1 on days 3 and 4; 4 mg of Compound 1 on days 5 and 6; 5 mg of Compound 1 on day 7; 6 mg of Compound 1 on day 8; 7 mg of Compound 1 on day 9; 8 mg of Compound 1 on day 10; and 9 mg of Compound 1 on day 11; followed by administering the maintenance dose of 10 mg of Compound 1 orally once daily from day 12 onwards.

5. The method of claim 1, wherein the disease or disorder is the rejection of a transplanted kidney.

6. A method as in claim 1, wherein the disease or disorder is the rejection of a transplanted liver.

7. A method as in claim 1, wherein the disease or disorder is the rejection of a transplanted heart.

8. A method as in claim 1, wherein the disease or disorder is the rejection of a transplanted lung.

9. A method as in claim 1, wherein the disease or disorder is rheumatoid arthritis.

10. A method as in claim 1, wherein the disease or disorder is psoriasis.

11. A method as in claim 1, wherein the disease or disorder is psoriatic arthritis.

12. A method as in claim 1, wherein the disease or disorder is Crohn's disease.

13. A method as in claim 1, wherein the disease or disorder is ulcerative colitis.

14. A method as in claim 1, wherein the disease or disorder is Hashimoto's thyroiditis.

15. A method as in claim 1, wherein the disease or disorder is atopic dermatitis.

* * * * *